US011915609B2

(12) United States Patent
Haga et al.

(10) Patent No.: US 11,915,609 B2
(45) Date of Patent: Feb. 27, 2024

(54) HOLLOW ORGAN MODEL UNIT AND METHOD FOR MANUFACTURING HOLLOW ORGAN MODEL UNIT

(71) Applicant: TOHOKU UNIVERSITY, Sendai (JP)

(72) Inventors: Yoichi Haga, Sendai (JP); Makoto Ohta, Sendai (JP); Yasutomo Shimizu, Sendai (JP); Tadao Matsunaga, Sendai (JP); Noriko Tsuruoka, Sendai (JP); Soyoka Osaki, Sendai (JP); Hiroshi Yoshida, Sendai (JP); Simon Andre Tupin, Sendai (JP); Kaihong Yu, Miyagi (JP)

(73) Assignee: TOHOKU UNIVERSITY, Sendai (JP)

( * ) Notice: Subject to any disclaimer, the term of this patent is extended or adjusted under 35 U.S.C. 154(b) by 1155 days.

(21) Appl. No.: 16/609,604

(22) PCT Filed: May 1, 2018

(86) PCT No.: PCT/JP2018/017454
§ 371 (c)(1),
(2) Date: Oct. 30, 2019

(87) PCT Pub. No.: WO2018/203561
PCT Pub. Date: Nov. 8, 2018

(65) Prior Publication Data

US 2020/0152091 A1 May 14, 2020

(30) Foreign Application Priority Data

May 2, 2017 (JP) ................................ 2017-091917

(51) Int. Cl.
*G09B 23/30* (2006.01)
*A61B 5/021* (2006.01)
*A61B 5/026* (2006.01)

(52) U.S. Cl.
CPC ............ *G09B 23/303* (2013.01); *A61B 5/021* (2013.01); *A61B 5/026* (2013.01)

(58) Field of Classification Search
None
See application file for complete search history.

(56) References Cited

U.S. PATENT DOCUMENTS 4,991,590 A * 2/1991 Shi ........................ G01L 9/0077 73/705
6,517,354 B1 * 2/2003 Levy ...................... G09B 23/28 434/262

(Continued)

FOREIGN PATENT DOCUMENTS

JP 2012203016 A 10/2012
JP 2013213986 A 10/2013

(Continued)

OTHER PUBLICATIONS

Office Action dated Apr. 1, 2021, in corresponding Chinese Patent Application No. 201880028220.1 and English translation of the Office Action. (16 pages).

(Continued)

*Primary Examiner* — James B Hull
(74) *Attorney, Agent, or Firm* — BUCHANAN INGERSOLL & ROONEY PC

(57) ABSTRACT

Provided is a hollow organ model unit. The hollow organ model unit includes a base that includes a recessed part, a hollow organ model that is placed in the recessed part, a filler that is filled in the recessed part, and a sensor that performs a measurement on the hollow organ model.

11 Claims, 15 Drawing Sheets

25
20
10
40
30
11
1

(56) References Cited

U.S. PATENT DOCUMENTS

| | | | | |
|---|---|---|---|---|
| 8,162,668 | B2 | 4/2012 | Toly | |
| 10,441,293 | B2 * | 10/2019 | Du | A61B 5/026 |
| 2011/0118564 | A1 * | 5/2011 | Sankai | A61B 5/417<br>600/301 |
| 2017/0032706 | A1 * | 2/2017 | Sekino | G09B 23/303 |
| 2017/0051736 | A1 * | 2/2017 | Okayama | F04B 49/22 |

FOREIGN PATENT DOCUMENTS

| | | | |
|---|---|---|---|
| JP | 2014092683 | A | 5/2014 |
| JP | 2015064487 | A | 4/2015 |
| JP | 2015-196075 | A | 11/2015 |
| JP | 2016057451 | A | 4/2016 |

OTHER PUBLICATIONS

Office Action (Notice of Reasons for Refusal) dated Apr. 5, 2022, in corresponding Japanese Patent Application No. 2019-515742 and English translation of the Office Action. (10 pages).
Office Action (Notice of Reasons for Refusal) dated Oct. 4, 2022, in corresponding Japanese Patent Application No. 2019-515742 and English translation of the Office Action. (10 pages).
International Search Report (PCT/ISA/210) dated Jul. 3, 2018, by the Japan Patent Office as the International Searching Authority for International Application No. PCT/JP2018/017454.
Written Opinion (PCT/ISA/237) dated Jul. 3, 2018, by the Japan Patent Office as the International Searching Authority for International Application No. PCT/JP2018/017454.

* cited by examiner

HOLLOW ORGAN MODEL UNIT AND METHOD FOR MANUFACTURING HOLLOW ORGAN MODEL UNIT

TECHNICAL FIELD

The present invention relates to a hollow organ model unit, or dummy, biomodel, phantom mock-up or tissue model unit, for use in training for treatment of a hollow organ or luminal organ, and a method for manufacturing a hollow organ model unit.

BACKGROUND ART

In the related art, lesions in hollow organs such as blood vessels are known to be treated from inside the lumens. In recent years, for example, treatment from inside the blood vessel without craniotomy has been increasingly performed for blocking blood flow into a cerebral aneurysm so that repture of the cerebral aneurysm can be prevented. A coil embolization operation, which is one of treatments performed from inside the blood vessel, includes inserting a catheter into a femoral artery to make approach to a lesion from inside the blood vessel and placing a platinum coil into a cerebral aneurysm through the catheter. This operation blocks blood flow into the cerebral aneurysm to prevent rupture of the cerebral aneurysm.

In an endovascular treatment, a doctor with a low skill level might damage a blood vessel by pressing a guide wire or a catheter against the blood vessel wall before it reaches the lesion. In a coil embolization operation, a doctor with a low skill level might place a coil at a biased position in an aneurysm or fail to sufficiently block blood flow at a neck portion, so that an insufficient treatment effect might be obtained. In general, doctors should gain experience in actural treatment of patients to improve their skill level, while training using a blood vessel model that mimics a blood vessel is known.

For example, PTL 1 proposes a catheter simulator with a mimic blood vessel flow path as a blood vessel model for use in training doctors. In the catheter simulator in PTL 1, a mimic blood flow path that mimics a blood vessel is formed on a thin plate made of aqueous gel of polyvinyl alcohol (PVA).

PRIOR ART LITERATURE

Patent Literature

PTL 1: JP-A-2014-92683

SUMMARY OF INVENTION

Technical Problem

The use of a blood vessel model is effective not only in training doctors as mentioned above but also in experiments for evaluating safety or effectiveness in the development of new methods or medical devices for endovascular treatment. Thus, it is desirable that doctors' skill levels or treatment effects can be quantitatively evaluated in training or experiments using a blood vessel model.

Thus, the invention has been made in view of the problems with the related art, and an object of the invention is to provide a hollow organ model unit capable of quantifying the skill level of doctors or the effect of treatment and to provide a method for manufacturing such a hollow organ model unit.

Solution to Problem

The hollow organ model unit according to the invention includes a base that has a recessed part, a hollow organ model that is placed in the recessed part, a filler that is filled in the recessed part, and a sensor that performs a measurement on a hollow organ model.

The method for manufacturing a hollow organ model unit according to the invention includes laminating a polyvinyl alcohol material and a sacrificial material to form a hollow organ model and a base, positioning a sensor midway through laminating the polyvinyl alcohol material and the sacrificial material, removing the sacrificial material, and filling a filler into a recessed part formed by removing the sacrificial material.

Advantageous Effects of Invention

According to the the invention mentioned above, the skill level of doctors and the effects of treatments can be quantitatively evaluated using the hollow organ model unit having the sensor provided to perform a measurement on a hollow organ model.

BRIEF DESCRIPTION OF DRAWINGS

FIG. 10 (*b*) shows an example of a measurement result of the displacement sensor in a state in which an inner wall of a bent portion of the blood vessel model is pressed by the catheter.

DESCRIPTION OF EMBODIMENTS

Hereinafter, a hollow organ model unit and a method for manufacturing the hollow organ model unit according to embodiments of the invention will be described. The blood vessel model unit in which a blood vessel is artificially reproduced as an example of a hollow organ and the method for manufacturing the blood vessel model unit will be described in the following embodiments.

First Embodiment

Figure 1:
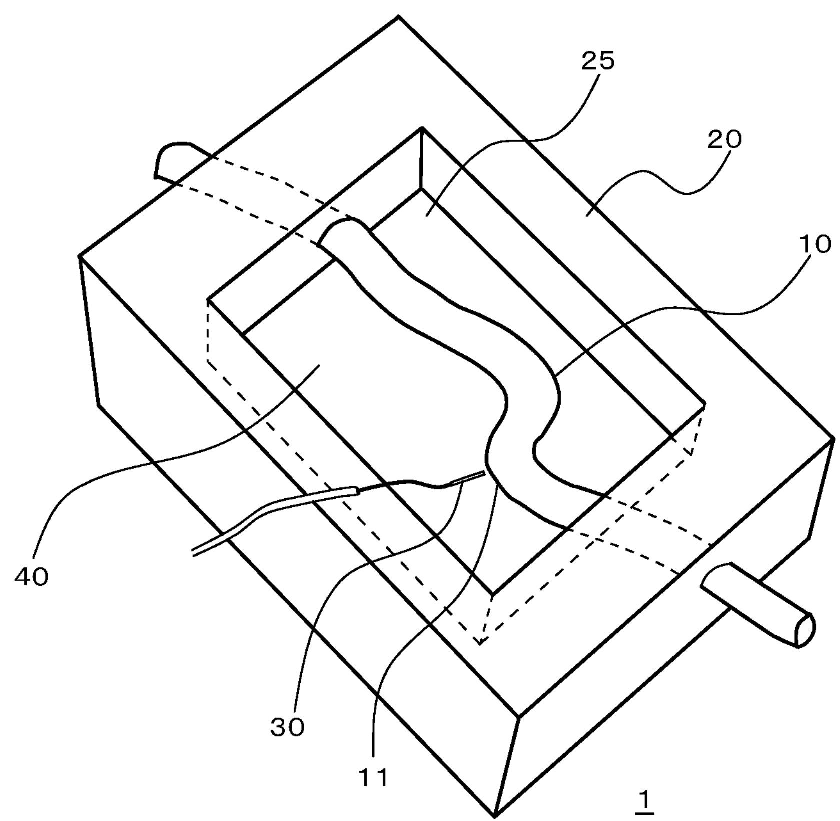
FIG. 1 is a perspective view of a blood vessel model unit according to a first embodiment.
Figure 2:
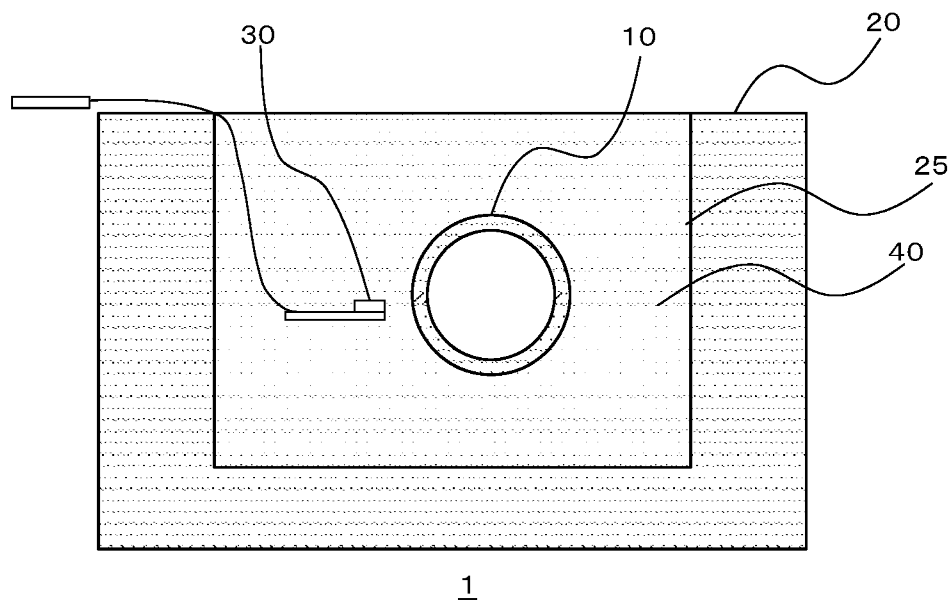
FIG. 2 is a schematic cross-sectional view of the blood vessel model unit according to the first embodiment.

FIG. 1 is a perspective view of a blood vessel model unit 1 according to the first embodiment. FIG. 2 is a schematic cross-sectional view of the blood vessel model unit 1 according to the first embodiment. As shown in FIGS. 1 and 2, the blood vessel model unit 1 has a rectangular parallelepiped shape, and includes a blood vessel model 10, a base 20, and a displacement sensor 30. A recessed part 25 is formed in the base 20, and a filler 40 is filled in the recessed part 25.

The blood vessel model 10 artificially reproduces a blood vessel. In order to reproduce a carotid artery and a cerebral artery, the shape and wall thickness of the blood vessel model 10 are the same as the shape and wall thickness of the carotid artery and the cerebral artery in the present embodiment. The blood vessel model 10 in the present embodiment is formed of an aqueous gel of polyvinyl alcohol (PVA). A friction of an inner wall of the blood vessel, a hardness of a blood vessel wall, and a shape of the blood vessel can be reproduced by forming the blood vessel model 10 with PVA. A concentration of PVA in the blood vessel model 10 is 10 wt % to 20 wt %, and is preferably 17 wt %. As shown in FIG. 1, the blood vessel model 10 has a bent portion 11 used for reproducing a siphon portion of the blood vessel.

The base 20 supports the blood vessel model 10 and the displacement sensor 30, and has a rectangular parallelepiped shape. Similar to the blood vessel model 10, the base 20 is formed of PVA with a concentration of 10 wt % to 20 wt %, preferably 17 wt %. The recessed part 25 having a rectangular parallelepiped shape is formed at the center of the base 20, and the filler 40 is filled in the recessed part 25. The filler 40 reproduces surrounding tissue of the blood vessel and is water or PVA. When PVA is used as the filler 40, the used PVA is softer than the blood vessel model 10, for example, PVA having a concentration of 2 wt % to 10 wt %, preferably 5 wt %. As shown in FIGS. 1 and 2, the bent portion 11 and the displacement sensor 30 of the blood vessel model 10 are disposed in the filler 40 in the recessed part 25.

Figure 3:
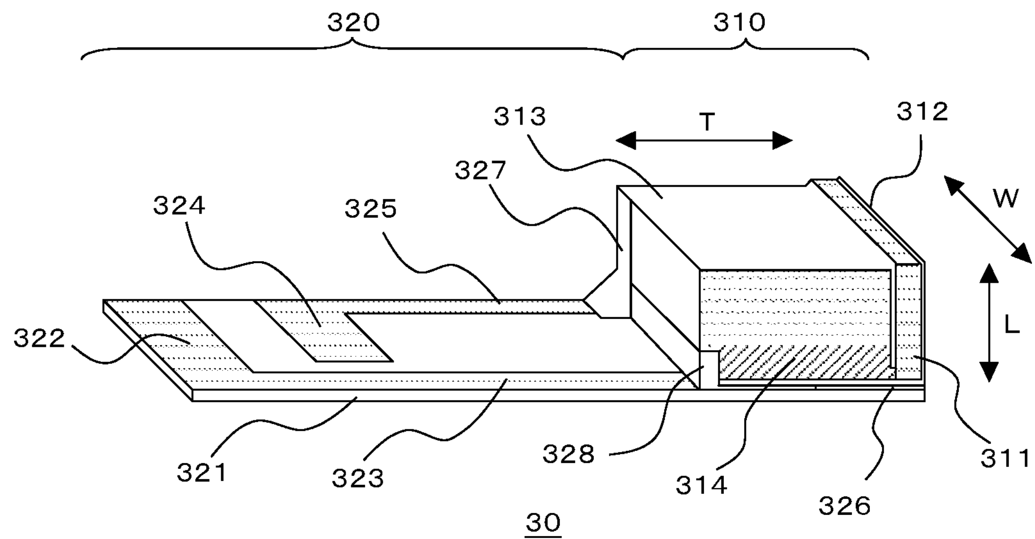
FIG. 3 is a perspective view of a displacement sensor according to the first embodiment.

The displacement sensor 30 measures a displacement of the blood vessel model 10. An example of the displacement sensor 30 includes an ultrasonic sensor according to the present embodiment. FIG. 3 is a perspective view of the displacement sensor 30 according to the present embodiment. As shown in FIG. 3, the displacement sensor 30 includes a sensor unit 310 and a wiring unit 320. The sensor unit 310 includes an ultrasonic transducer 311, a first electrode 312 and a second electrode 313 that cover the ultrasonic transducer 311, and a backing 314.

The ultrasonic transducer 311 transmits ultrasonic waves and receives reflected waves of the ultrasonic waves, and is, for example, a piezoelectric single crystal of magnesium niobate and lead titanate (PMT-PT) having electromechanical coupling higher than lead zirconate titanate (PZT). The ultrasonic transducer 311 has a thickness of about 96 μm, a width W of about 1.0 mm, and a length L of about 0.5 mm.

The first electrode 312 and the second electrode 313 are Au/Cr electrodes which are formed by using chromium (Cr) as a substrate and coating gold (Au) on the substrate. The first electrode 312 and the second electrode 313 cover a front side and a rear side of the ultrasonic transducer 311. The backing 314 is a damping member that attenuates undesired vibration of the ultrasonic transducer 311 and shortens a pulse width of the ultrasonic waves. The backing 314 is formed of a mixture of epoxy resin and tungsten powder. A thickness T of the backing 314 is about 1.3 mm and is larger than a wavelength of the ultrasonic waves.

The wiring unit 320 includes a film 321, a first electrode pad 322, a first wire 323, a second electrode pad 324, and a second wire 325. The first electrode pad 322, the first wire 323, the second electrode pad 324, and the second wire 325 are formed on the film 321. The wiring unit 320 includes a first conductive material 326 that connects the first wire 323 and the first electrode 312, a second conductive material 327 that connects the second wire 325 and the second electrode 313, and an insulating material 328 that is placed between the first electrode 312 and the second electrode 313 and isolates the first electrode 312 and the second electrode 313. Further, coaxial cables (not shown) are soldered to the first electrode pad 322 and the second electrode pad 324, respectively.

The film 321 is a polyimide film, and has a thickness of about 25 μm and a length of about 30 mm. By using a flexible polyimide film in the displacement sensor 30, it is easy to position the displacement sensor 30. The first electrode pad 322, the first wire 323, the second electrode pad 324, and the second wire 325 are copper foils formed on the film 321. The first conductive material 326 and the second conductive material 327 are formed of conductive epoxy resin, and the insulating material 328 is formed of insulating epoxy resin. Materials and sizes of the above respective parts in the displacement sensor 30 are examples, and the invention is not limited thereto. Although the ultrasonic transducer 311 in the displacement sensor 30 in FIG. 3 is caused to vibrate in a front-back direction and transmits ultrasonic waves from a front surface, the invention is not limited thereto. For example, the ultrasonic transducer 311 may be caused to vibrate in an upper-lower direction, and may transmit ultrasonic waves from an upper surface.

Figure 4:
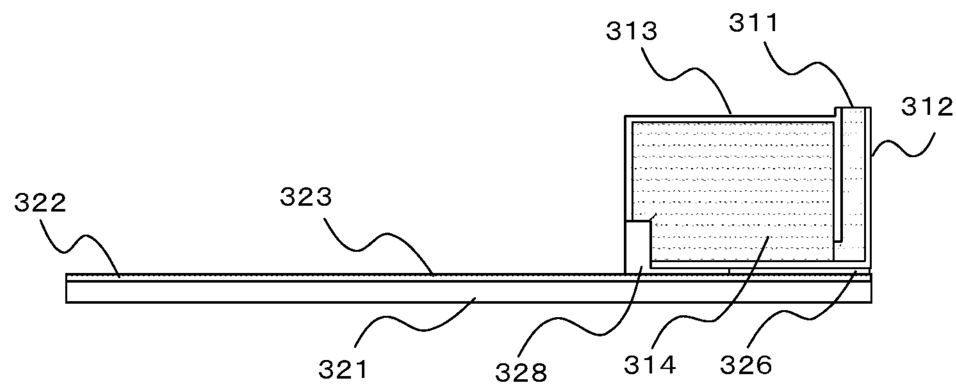
FIG. 4 is an end view of the displacement sensor at a first wire side.
Figure 5:
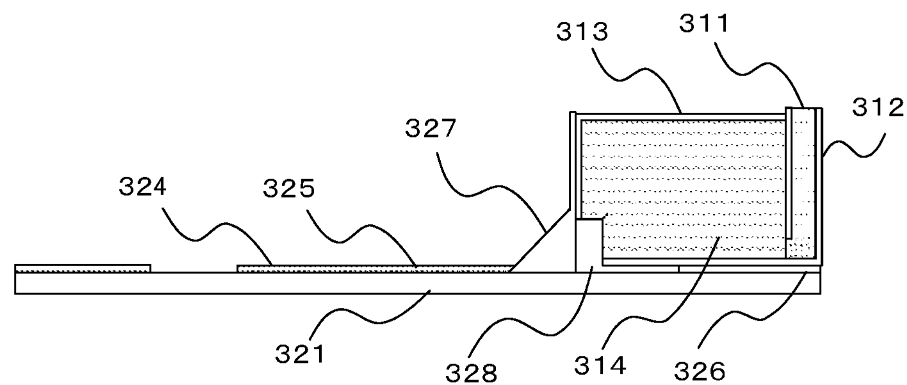
FIG. 5 is an end view of the displacement sensor at a second wire side.

FIG. 4 is an end view of the displacement sensor 30 at a first wire 323 side. FIG. 5 is an end view of the displacement sensor 30 at a second wire 325 side. As shown in FIG. 4, the first electrode 312 extends from the front surface of the ultrasonic transducer 311 to a bottom surface of the backing 314, and is connected to the first wire 323 and the first electrode pad 322 via the first conductive material 326. As shown in FIG. 5, the second electrode 313 extends from a rear surface of the ultrasonic transducer 311 to an upper surface of the backing 314, and is connected to the second wire 325 and the second electrode pad 324 via the second conductive material 327.

Figure 6:
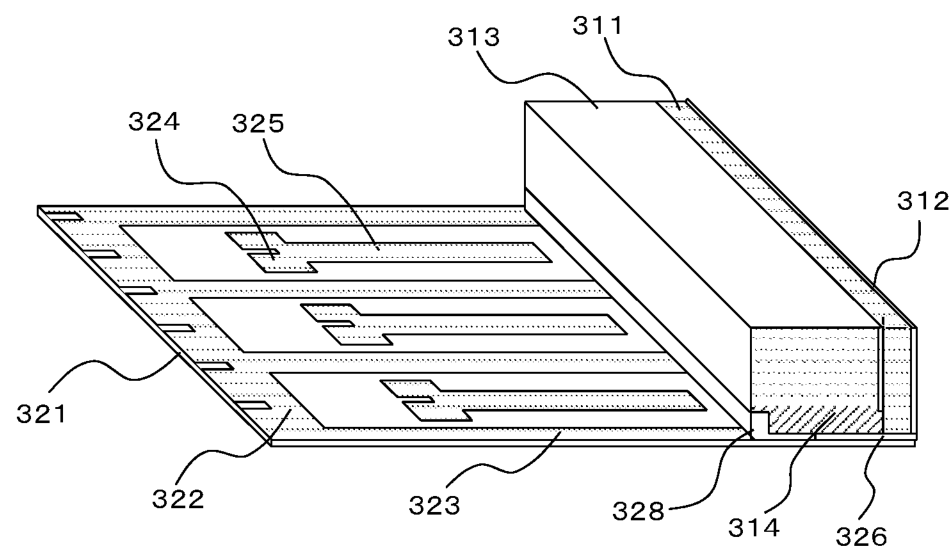
FIG. 6 is a diagram showing a method for manufacturing the displacement sensor according to the first embodiment.
Figure 7:
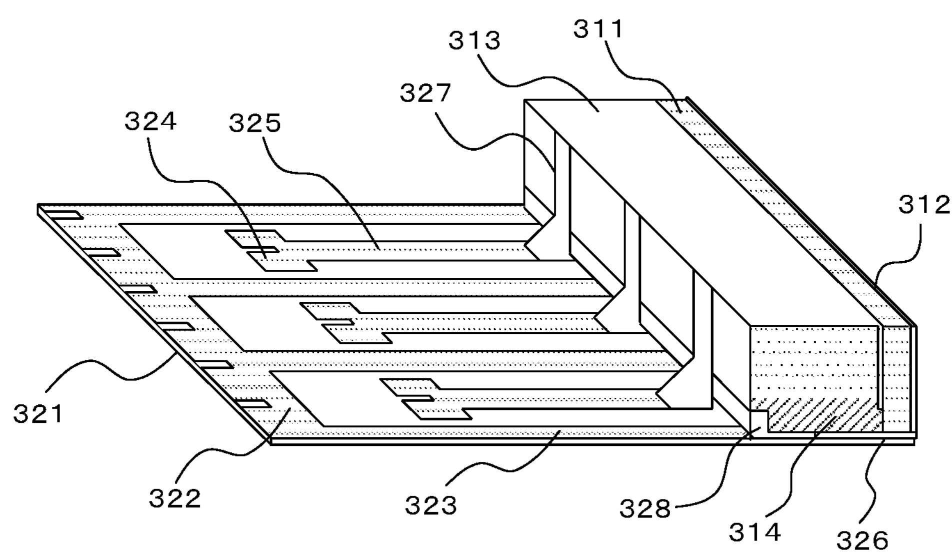
FIG. 7 is a diagram showing the method for manufacturing the displacement sensor according to the first embodiment.

FIGS. 6 and 7 are diagrams showing a method for manufacturing the displacement sensor 30 according to the present embodiment. First, as shown in FIG. 6, the long ultrasonic transducer 311, the first electrode 312, the second electrode 313, the backing 314, the first conductive material 326, and the insulating material 328 are bonded to the film 321 on which a plurality of first electrode pads 322, first wires 323, second electrode pads 324, and second wires 325 are continuously formed. Then, as shown in FIG. 7, the second conductive material 327 is bonded to each of the second wires 325, and then one displacement sensor 30 is formed by cutting into strips. The displacement sensor 30 is manufactured in such a manner to improve manufacturing efficiency.

Figure 8:
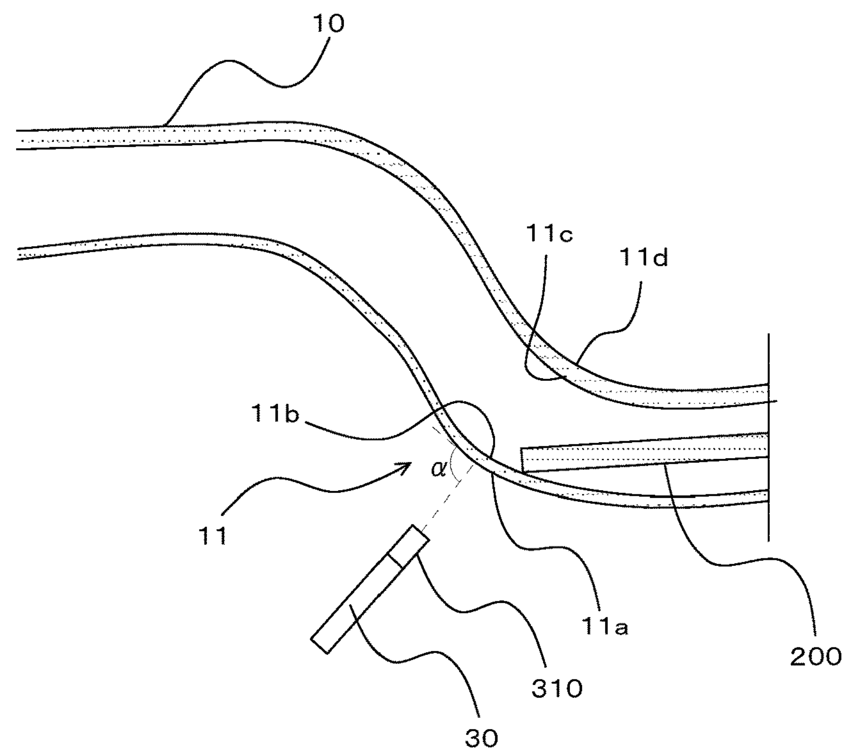
FIG. 8 is a diagram showing a measurement position of a blood vessel model measured by the displacement sensor.

When inserting a catheter into a blood vessel, a doctor with a low skill level usually tends to accidentally press the catheter against the blood vessel wall at a bent portion such as a siphon portion of the blood vessel. Thus, the displacement sensor 30 according to the present embodiment measures the displacement of the bent portion 11 of the blood vessel model 10. FIG. 8 is a diagram illustrating a measurement position of the blood vessel model 10 measured by the displacement sensor 30. As shown in FIG. 8, the displacement sensor 30 is placed outside the bent portion 11 of the blood vessel model 10 and is separated away from the bent portion 11. A distance between the bent portion 11 and the ultrasonic transducer 311 in the displacement sensor 30 is, for example, 1 mm to 15 mm. Thus, the displacement sensor 30 can be separated away from the blood vessel model 10 by using an ultrasonic sensor as the displacement sensor 30. Accordingly, the displacement can be measured without affecting physical properties of the blood vessel model 10 as compared with a case in which a contact displacement sensor is bonded to the blood vessel model 10. The displacement sensor 30 is placed such that an angle $\alpha$ between a first outer wall 11*a* of the bent portion 11 and a plane perpendicular to a front end surface of the sensor part 310 is 90 degrees. Accordingly, reflection intensity can be increased and a reflection echo can be accurately measured.

The displacement sensor 30 transmits ultrasonic waves to the bent portion 11, and receives reflection echoes from the first outer wall 11*a*, a first inner wall 11*b*, a second inner wall 11*c*, and a second outer wall 11*d* of the bent portion 11. Then distances between the displacement sensor 30 and the first outer wall 11*a*, the first inner wall 11*b*, the second inner wall 11*c*, and the second outer wall 11*d* can be calculated based on the received reflection echoes.

Figure 9:
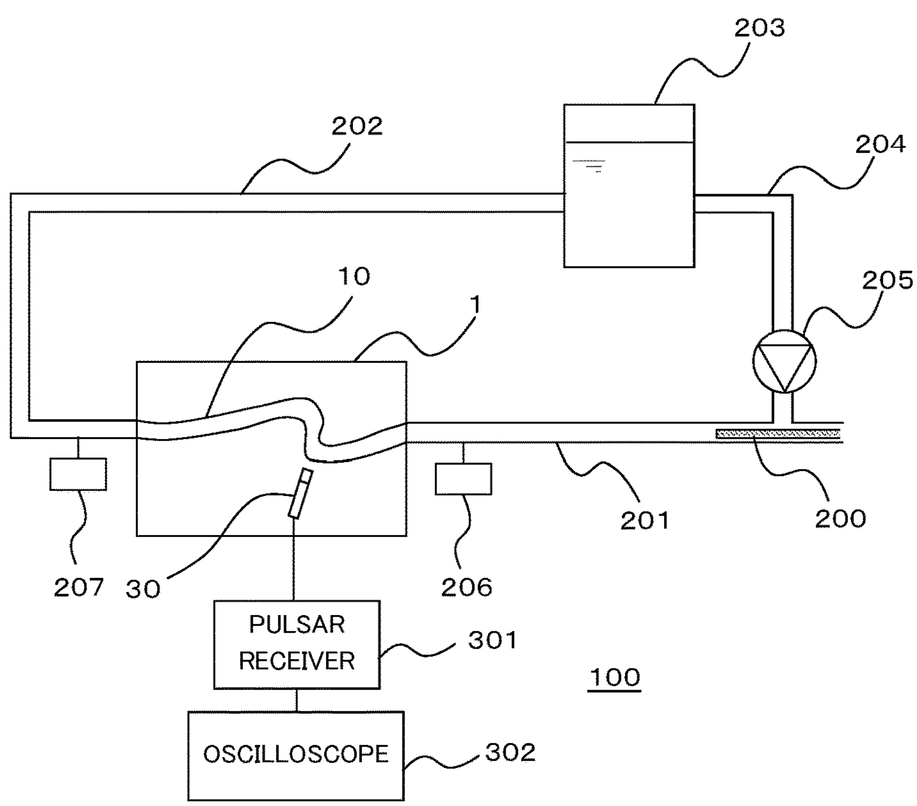
FIG. 9 is a schematic configuration diagram of a measurement system using the blood vessel model unit according to the first embodiment.

FIG. 9 is a schematic configuration diagram of a measurement system 100 using the blood vessel model unit 1 according to the present embodiment. As shown in FIG. 9, the measurement system 100 includes the blood vessel model unit 1, an insertion pipe 201 connected to an inlet of the blood vessel model 10 in the blood vessel model unit 1, a first pipe 202 connected to an outlet of the blood vessel model 10, a water storage unit 203 that stores water to be circulated in the blood vessel model 10, and a second pipe 204 connecting the water storage unit 203 and the insertion pipe 201. Length of the insertion pipe 201 is set by assuming that a catheter 200 is inserted from a femoral artery of a thigh, so that operability can be reproduced. The measurement system. 100 includes a pump 205 that controls a flow rate of water flowing in the blood vessel model 10, an inlet sensor 206 that measures a water pressure at an inlet side of the blood vessel model 10, an outlet sensor 207 that measures a water pressure at an outlet side of the blood vessel model 10, a pulsar receiver 301 that is connected to the displacement sensor 30 and transmits and receives ultrasonic waves, and an oscilloscope 302 that displays a measurement result.

When a measurement is performed in the measurement system 100, the pump 205 circulates water in the water storage unit 203 in an order of the second pipe 204, the insertion pipe 201, the blood vessel model 10, and the first pipe 202. The water pressure at this time is controlled based on measurement results of the inlet sensor 206 and the outlet sensor 207 so as to be substantially the same as a blood pressure. In order to keep the blood vessel model unit 1 formed of PVA in a cooled state, the measurement is preferably performed in a low-temperature environment or temperature of the circulated water is preferably a low temperature. Then displacement is measured by the displacement sensor 30 when the catheter 200 that is inserted from an end portion of the insertion pipe 201 passes through the blood vessel model 10.

Figure 10A:
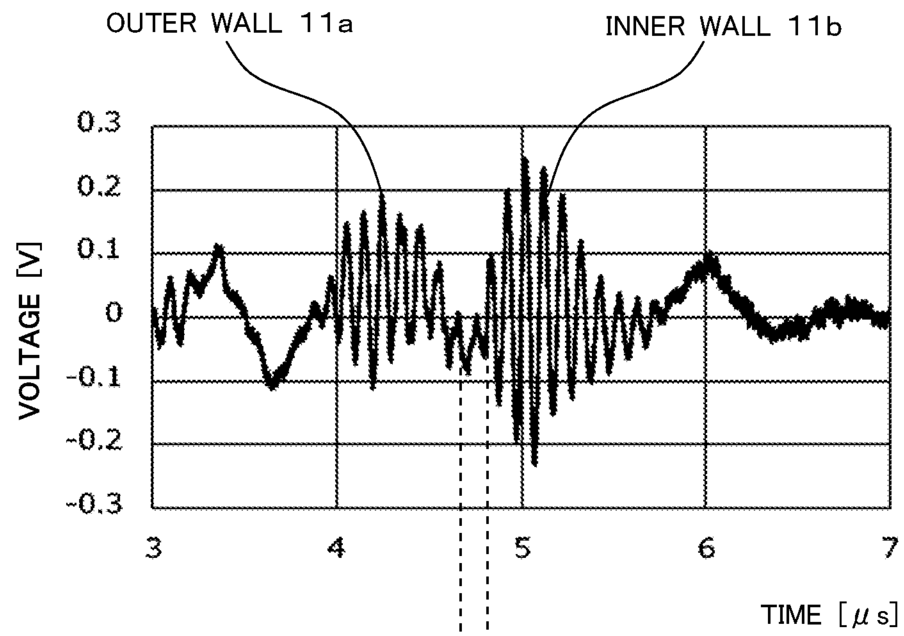
FIG. 10(*a*) shows an example of a measurement result of the displacement sensor in a state in which a catheter is not inserted into the blood vessel model.
Figure 10B:
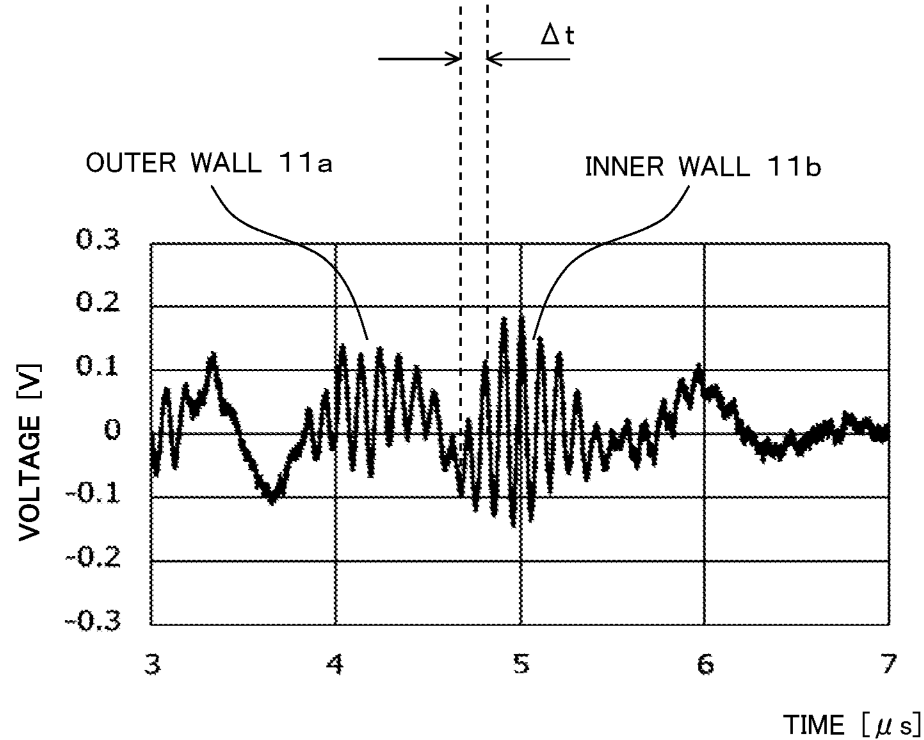

FIG. 10(*a*) shows an example of a measurement result of the displacement sensor 30 in a state in which the catheter 200 is not inserted into the blood vessel model 10. FIG. 10(*b*) shows an example of a measurement result of the displacement sensor 30 in a state in which an inner wall of the bent portion 11 of the blood vessel model 10 is pressed by the catheter 200. As shown in FIGS. 10(*a*) and 10(*b*), the displacement of the bent portion 11 can be known from the shifting of echoes reflected from the first outer wall 11*a* and the first inner wall 11*b* of the bent portion 11. The amount $\Delta L$ of displacement of the blood vessel model 10 can be calculated from the following equation (1) using a shift time $\Delta t$ after the displacement.

$$\Delta L=(\Delta t\times C)/2 \tag{1}$$

"C" in the equation (1) is the speed of sound in water, which is about 1500 m/s.

For example, when the shift time $\Delta t$ is 0.114 μs after the displacement with respect to the signal before the displacement, the amount $\Delta L$ of displacement of the blood vessel model 10 is 0.086 mm.

Thus, when the displacement of the blood vessel model 10 is measured, not only a doctor's feeling but also an actual load on the blood vessel can be quantified as the amount of displacement. As a result, the doctor's skill level can be evaluated or a treatment effect can be checked in an objective manner. For example, when the displacement amount is larger than a predetermined reference value, the doctor's skill level may be evaluated as low, which allows further training to continue. When a simulation is performed using the blood vessel model 10 before an operation and the actual load on the blood vessel is measured, an objectively safer treatment method can also be proposed.

Figure 11:
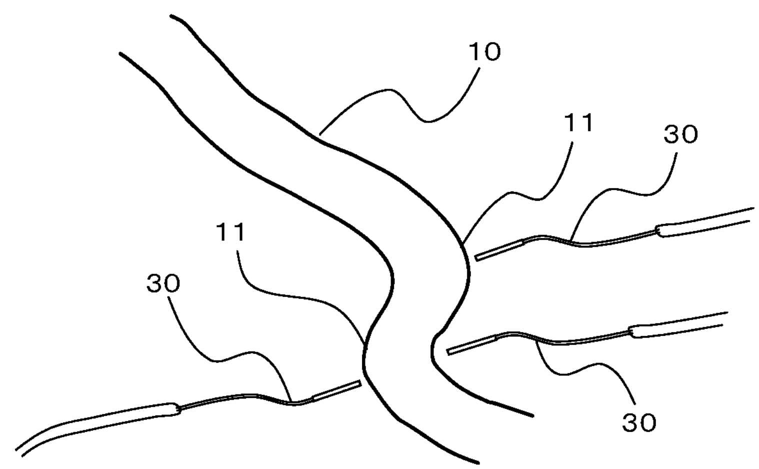
FIG. 11 is a diagram showing a blood vessel model unit including a plurality of displacement sensors according to a modification.
Figure 12:
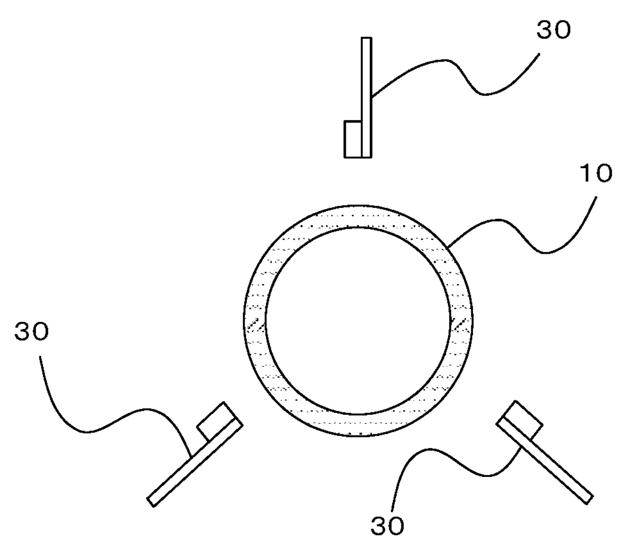
FIG. 12 is a diagram showing a blood vessel model unit including a plurality of displacement sensors according to a modification.

The blood vessel model unit 1 may include a plurality of displacement sensors 30. FIGS. 11 and 12 are diagrams showing modifications of the blood vessel model unit 1 including the plurality of displacement sensors 30. For example, each of a plurality of bent portions 11 may be provided with the displacement sensor 30 as shown in FIG. 11. Alternatively, the displacement sensor 30 may be provided at a recessed side of the bent portion 11 or a position other than the bent portion 11 to measure a displacement of each part. As shown in FIG. 12, a plurality of displacement sensors 30 may be provided in a circumferential direction of the blood vessel model 10. With such a configuration, a direction of applying the catheter 200 or the like in the blood vessel model 10 can be measured. In particular, it is possible to know in detail how the blood vessel model 10 is displaced by providing the plurality of displacement sensors 30 in positions that are considered to be important in the blood vessel model 10.

Figure 13:
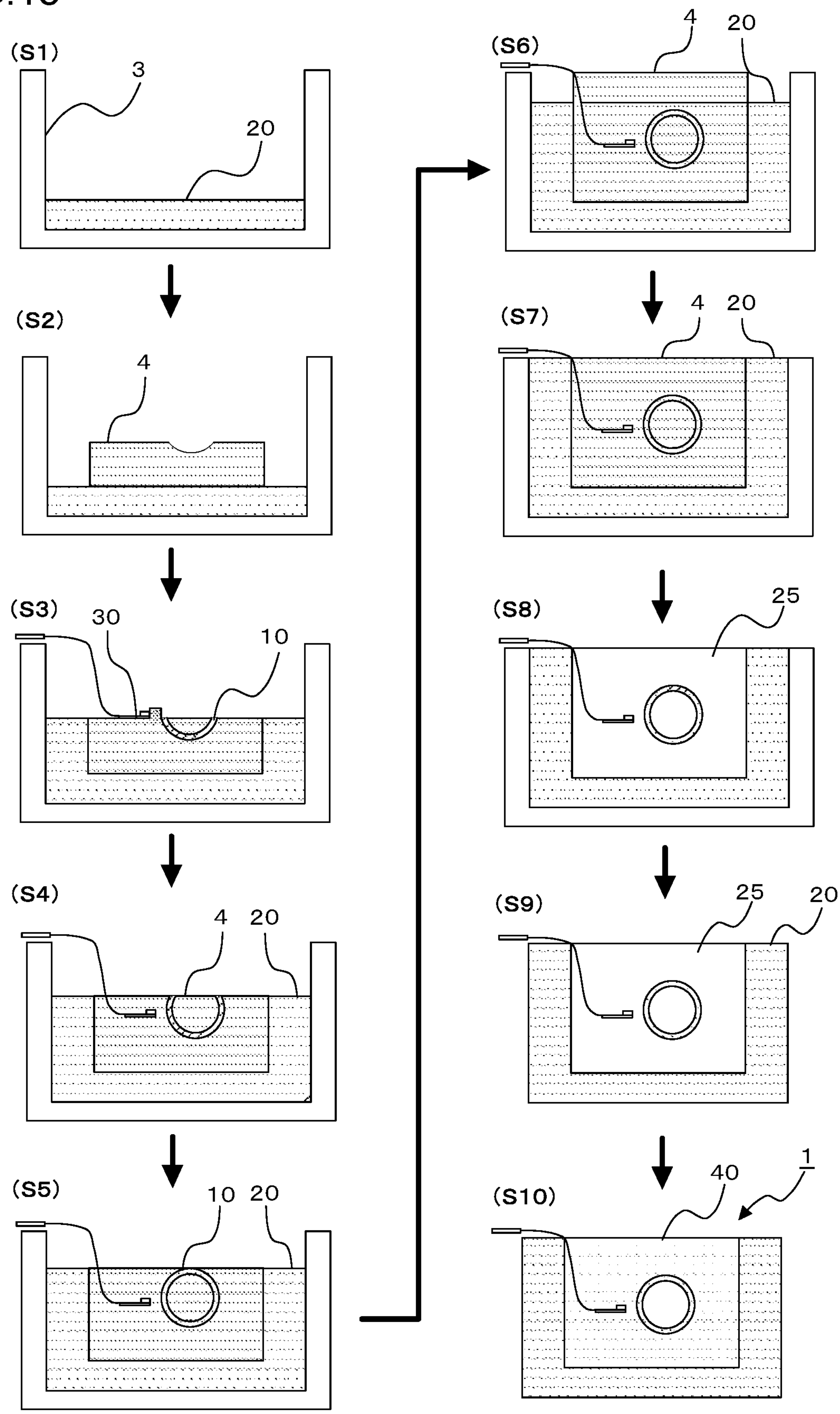
FIG. 13 is a schematic cross-sectional view showing a flow of a method for manufacturing the blood vessel model unit according to the first embodiment.

Next, a method for manufacturing the blood vessel model unit 1 according to the present embodiment will be described. FIG. 13 is a schematic cross-sectional view showing a flow of a method for manufacturing the blood vessel model unit 1 according to the present embodiment. The blood vessel model unit 1 according to the present embodiment is manufactured by laminating a sacrificial material 4 and PVA that has a concentration of about 17 wt % and serves as a material of the blood vessel model 10 and the base 20 by using a 3D printer. Examples of the sacrificial material 4 include a wax, limonene, polyethylene glycol (PEG), water-soluble PVA, and the like.

First, PVA is laminated in a box-shaped mold frame 3 (S1). The sacrificial material 4 that serves as a frame used for forming the blood vessel model 10 thereon is laminated on PVA (S2). PVA is heated at the time of being discharged so as to acquire flowability. PVA is injected amid the sacrificial material 4 and is surrounded by the sacrificial material 4 so as to be prevented from deformation. Then, the displacement sensor 30 is placed at the measurement position of the blood vessel model 10 (S3). At this time, a position of a front end surface of the displacement sensor 30 is regulated by the sacrificial material 4 as shown in FIG. 13, so that it is easy to position the displacement sensor 30. Specifically, a distance between the displacement sensor 30 and the blood vessel model 10 can be set to a predetermined distance and an angle of the displacement sensor 30 can be set to a predetermined angle by placing the front end face of the displacement sensor 30 against the sacrificial material 4. Then, lamination of PVA and the sacrificial material 4 is repeated (S4 to S7) to form the blood vessel model 10. Thereafter, the sacrificial material 4 is removed (S8), and the base 20 is taken out from the mold frame 3 (S9). Finally, the filler 40 is filled in the recessed part 25 formed by removing the sacrificial material 4 (S10). As a result, the blood vessel model unit 1 is manufactured.

Thus, the blood vessel model unit 1 can be easily manufactured by laminating PVA and the sacrificial material 4 using the 3D printer. In particular, when a plurality of displacement sensors 30 are provided, each of the displacement sensors 30 can be easily positioned by using the sacrificial material 4 to dispose the displacement sensor 30 when laminating PVA and the sacrificial material 4. In addition, blood vessels with complicated shapes and bending of blood vessels can be reproduced using the 3D printer. Accordingly, the blood vessel model unit 1 that reproduces a patient's blood vessels can be manufactured and a personalized medical care can be achieved.

Figure 14:
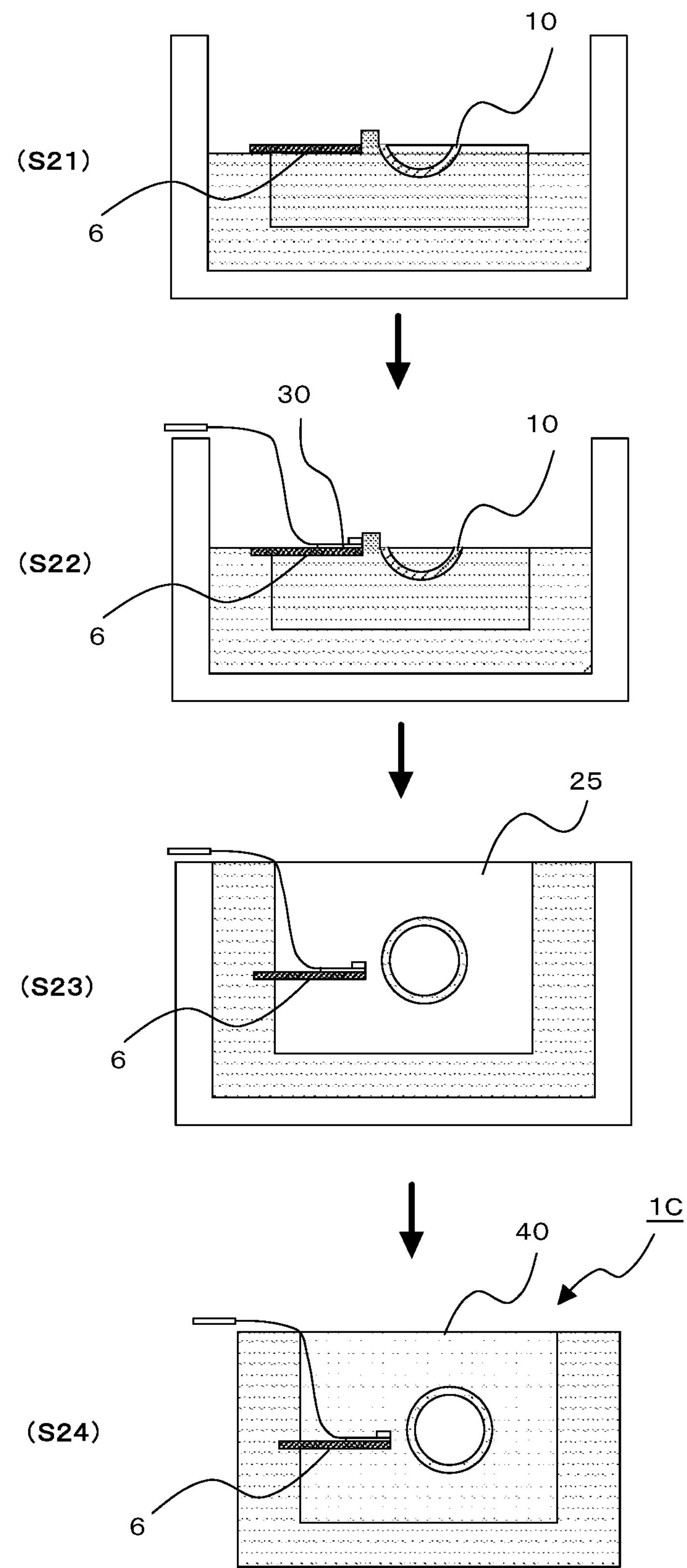
FIG. 14 is a schematic cross-sectional view showing a flow of a method for manufacturing a blood vessel model unit according to a modification of the first embodiment.

Although the sacrificial material 4 is entirely removed in the example in FIG. 13, the invention is not limited thereto. For example, a sacrificial material used for positioning the displacement sensor 30 may be left as a support material 6. FIG. 14 is a schematic cross-sectional view showing a flow of a method for manufacturing the blood vessel model unit 1 according to a modification of the first embodiment. As shown in FIG. 14, when manufacturing the blood vessel model unit 1, the support material 6 used for supporting the displacement sensor 30 is placed (S21). Then, the displacement sensor 30 is placed on the support material 6 (S22). The support material 6 uses a material different from the sacrificial material 4. For example, the support material 6 is PVA having a concentration of about 17 wt %.

Thereafter, PVA and the sacrificial material 4 are laminated, and then the sacrificial material 4 is removed (S23). At this time, the support material 6 is left as shown in FIG. 14, and the displacement sensor 30 is supported by the support material 6. Then, the filler 40 is filled into the recessed part 25, and the blood vessel model unit 1 is manufactured (S24). Alternatively, the support material 6 may be provided to not only support the displacement sensor 30, but also support the blood vessel model 10. That is, the blood vessel model unit 1 according to the modification includes the blood vessel model 10, the base 20, the displacement sensor 30, the filler 40, and the support material 6 that supports the blood vessel model or the displacement sensor 30. Accordingly, the displacement sensor 30 can be prevented from displacement, a measurement error caused by the displacement can be prevented from occurring, and the blood vessel model 10 can be prevented from deformation.

Figure 15:
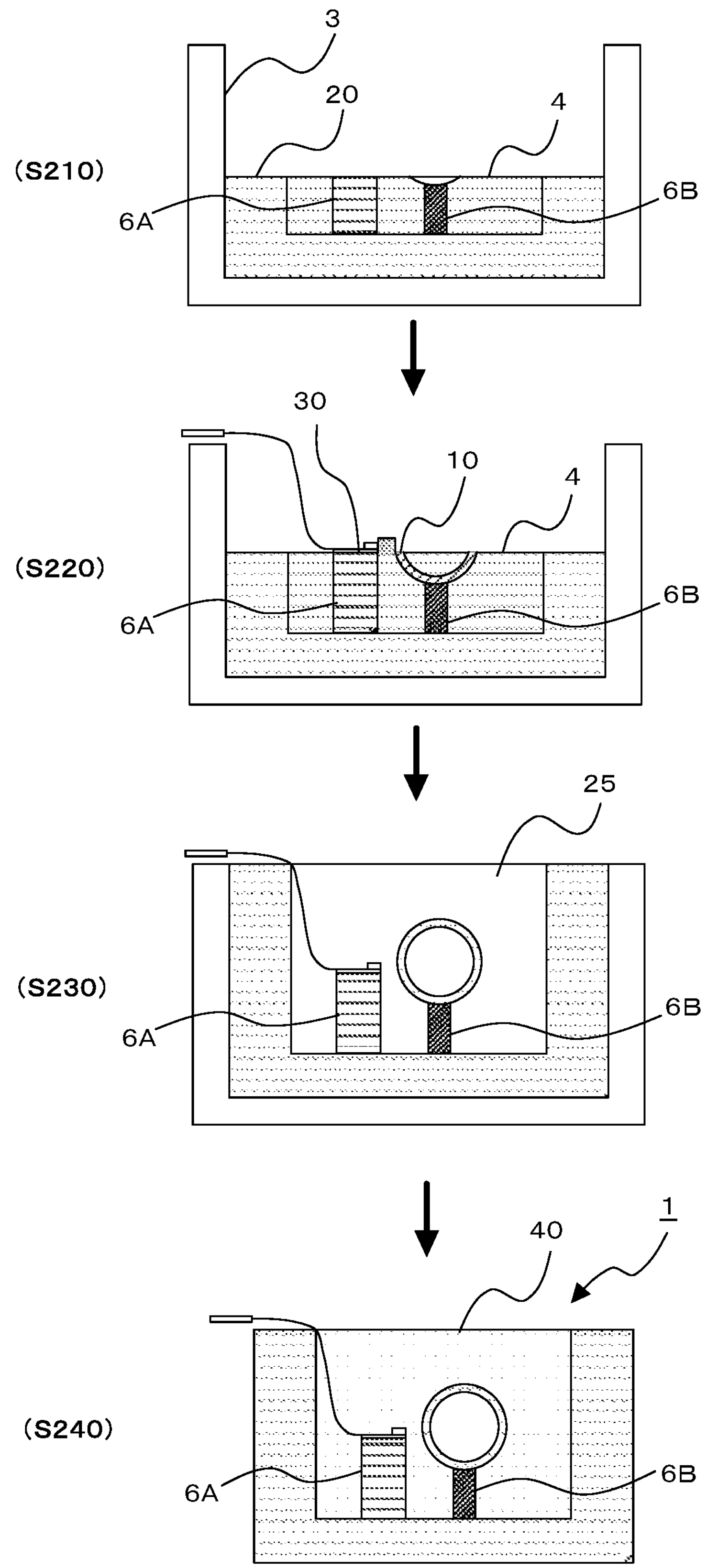
FIG. 15 is a schematic cross-sectional view showing a flow of a method for manufacturing a blood vessel model unit according to another modification of the first embodiment.

FIG. 15 is a schematic cross-sectional view showing a flow of a method for manufacturing the blood vessel model unit 1 according to another modification of the first embodiment. FIG. 15 shows a method for manufacturing the blood vessel model unit 1 that includes the support material 6 supporting the blood vessel model 10 and the displacement sensor 30 from below. As shown in FIG. 15, PVA is laminated in the mold frame 3, and the sacrificial material 4 serving as a frame used for forming the blood vessel model 10, a support material 6A that supports the displacement sensor 30, and a support material 6B that supports the blood vessel model 10 are laminated on the PVA (S210). Then, the displacement sensor 30 is placed on the support material 6A, and the blood vessel model 10 is formed on the support material 6B (S220).

Thereafter, PVA and the sacrificial material 4 are laminated, and then the sacrificial material 4 is removed (S230). At this time, the support materials 6A and 6B are left as shown in FIG. 15. The blood vessel model 10 and the displacement sensor 30 are supported by the support materials 6A and 6B from below. Then, the filler 40 is filled into the recessed part 25, and the blood vessel model unit 1 is manufactured (S240).

Second Embodiment

Next, a second embodiment according to the invention will be described. The second embodiment is different from the first embodiment in terms of a shape of a blood vessel model and including a pressure sensor instead of the displacement sensor 30. Other configurations of the blood vessel model unit are the same as the configurations in the first embodiment, and are denoted by the same reference numerals.

Figure 16:
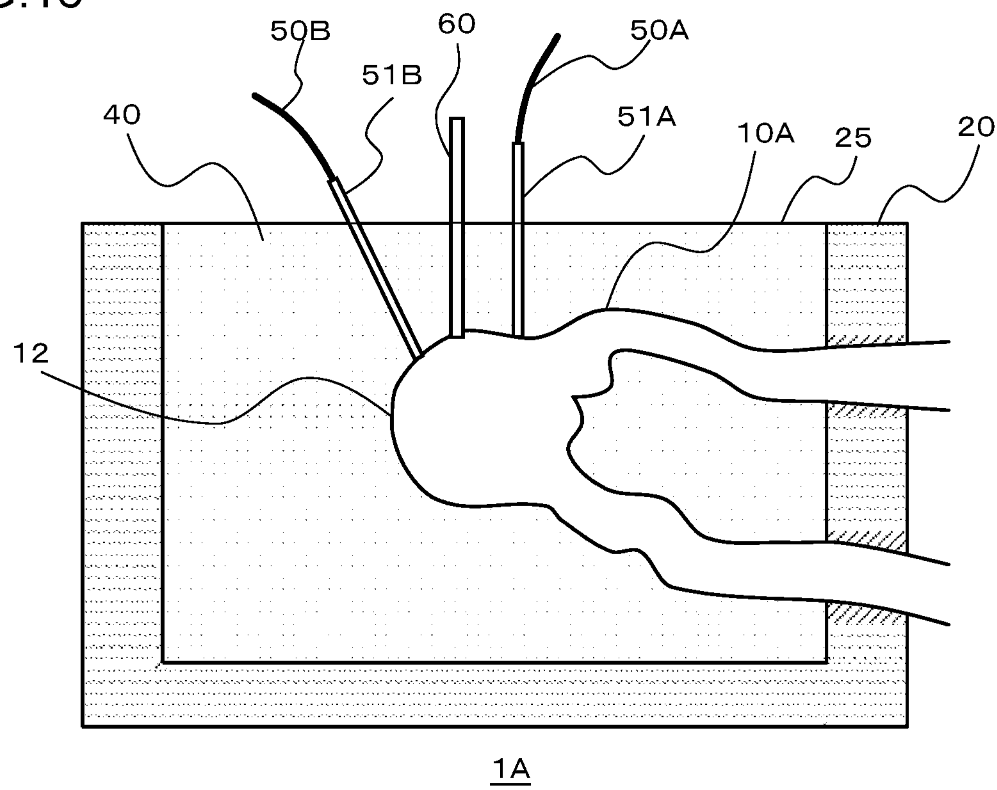
FIG. 16 is a schematic cross-sectional view of a blood vessel model unit according to a second embodiment.

FIG. 16 is a schematic cross-sectional view of a blood vessel model unit 1A according to the second embodiment. The blood vessel model unit 1A according to the present embodiment is used for a training or an experiment of a coil embolization operation for preventing blood from flowing into a cerebral aneurysm. As shown in FIG. 16, a blood vessel model 10A in the blood vessel model unit 1A according to the present embodiment includes the aneurysm-like portion 12 that reproduces the cerebral aneurysm. The aneurysm-like portion 12 is hollow inside and has a spherical shape having a diameter of about 6 mm. The blood vessel model unit 1A according to the present embodiment includes a first pressure sensor 50A and a second pressure sensor 50B used for measuring a pressure in the aneurysm-like portion 12, a first tube 51A and a second tube 51B into which the first pressure sensor 50A and the second pressure sensor 50B are respectively inserted, and an air discharging tube 60 used for discharging air accumulated in the aneurysm-like portion 12.

Figure 17:
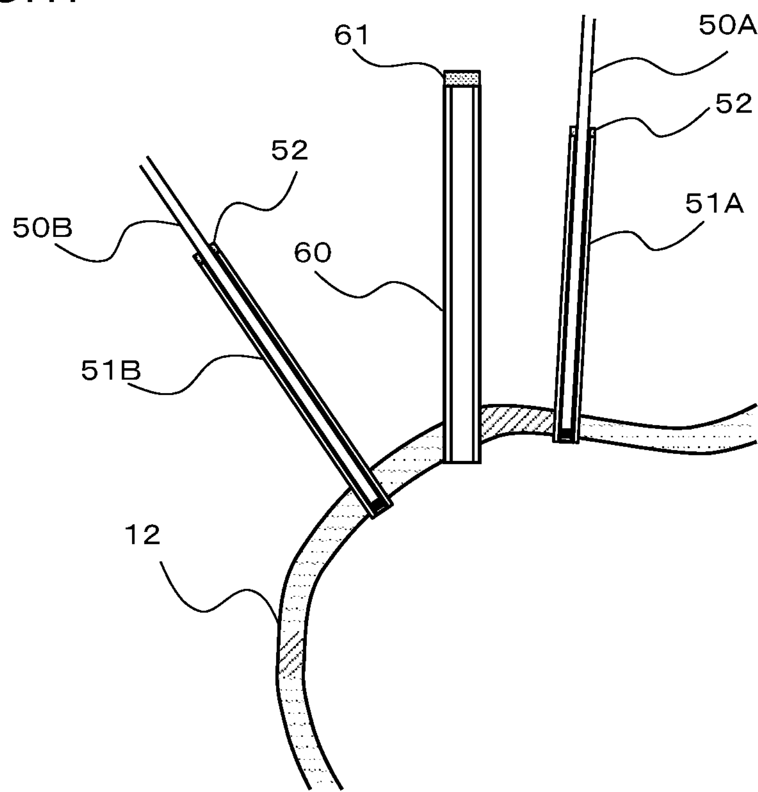
FIG. 17 is an enlarged cross-sectional view of a periphery of an aneurysm-like portion of a blood vessel model according to the second embodiment.

FIG. 17 is an enlarged schematic cross-sectional view of a periphery of the aneurysm-like portion 12 of the blood vessel model 10A. As shown in FIG. 17, end portions at one side of the first tube 51A and the second tube 51B pass through a wall of the aneurysm-like portion 12 and protrude towards an inner side of the aneurysm-like portion 12. Here, when a protruding amount of the first tube 51A and the second tube 51B is large, a turbulent flow occurs inside the aneurysm-like portion 12, or the end portions may collide with the catheter 200 or the like. On the other hand, when the first tube 51A and the second tube 51B do not reach an inner wall of the aneurysm-like portion 12, the first pressure sensor 50A and the second pressure sensor 50B cannot accurately measure the pressure in the aneurysm-like portion 12. Therefore, the protruding amount of the first pressure sensor 50A and the second pressure sensor 50B is set to 0 mm to about 0.5 mm considering the above problem. The first tube 51A and the second tube 51B are thin-walled polymer tubes. A polyimide tube having an inner diameter of about 200 μm and an outer diameter of about 240 μm is used in the present embodiment.

The first pressure sensor 50A and the second pressure sensor 50B are respectively inserted from end portions at the other side of the first tube 51A and the second tube 51B. When the first pressure sensor 50A and the second pressure sensor 50B are inserted, the end portions at the other side of the first tube 51A and the second tube 51B are sealed with hot bonds 52, so that the first pressure sensor 50A and the second pressure sensor 50B can be fixed, and water can be prevented from leaking from an inside of the aneurysm-like portion 12. Further, the first pressure sensor 50A and the second pressure sensor 50B can be freely inserted and removed using the hot bond 52. When a coil embolization operation is performed in the aneurysm-like portion 12, the first pressure sensor 50A and the second pressure sensor 50B are disposed in a place where it is difficult for the coil to enter, or a place desired to be embolized securely.

Similar to the first tube 51A and the second tube 51B, an end portion at one side of the air discharging tube 60 passes through a wall of the aneurysm-like portion 12. The air discharging tube 60 is a thin-walled polymer tube. A polyimide tube having an inner diameter of about 800 μm is used in the present embodiment. An end portion at the other side of the air discharging tube 60 is sealed with a hot bond 61 and is opened when it is necessary to discharge air. In other places in the aneurysm-like portion 12 and the blood vessel model 10A, the air discharging tube 60 may be disposed at a place where air is likely to accumulate.

Figure 18:
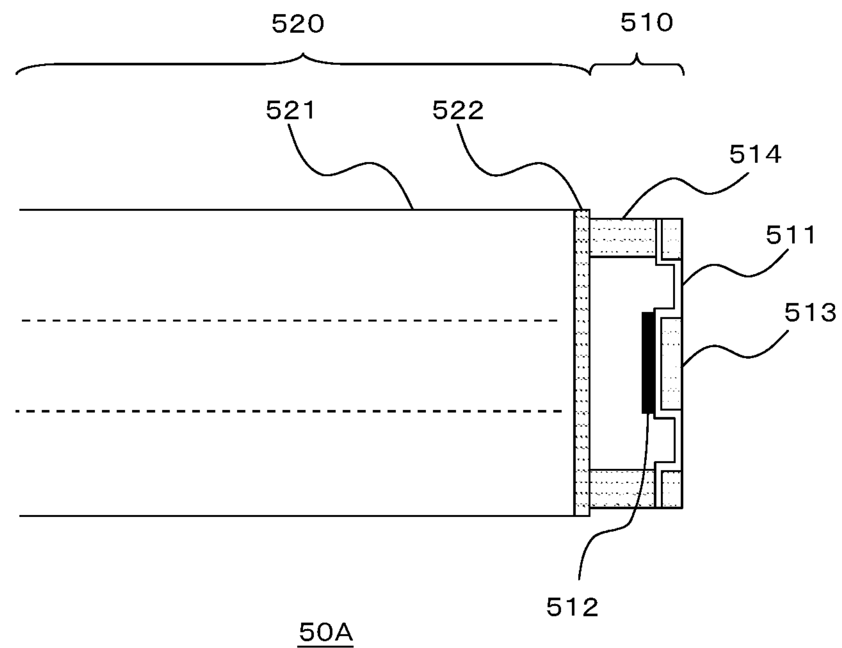
FIG. 18 is a diagram showing a structure of a pressure sensor according to the second embodiment.

The first pressure sensor 50A and the second pressure sensor 50B according to the present embodiment are fiber-optic pressure sensors. FIG. 18 is a diagram showing a structure of the first pressure sensor 50A according to the present embodiment. A configuration of the second pressure sensor 50B is the same as a configuration of the first pressure sensor 50A. As shown in FIG. 18, the first pressure sensor 50A includes a pressure receiving portion 510 and an optical fiber portion 520. The optical fiber portion 520 includes a graded index multi-mode optical fiber 521 having a cladding diameter of 125 μm and a core diameter of 50 μm, and a chromium (Cr) thin film half mirror 522 formed at a tip of the optical fiber 521. The pressure receiving portion 510 is a sensor chip having a cylindrical shape with a diameter of 120 μm, and is bonded to an end surface of the optical fiber portion 520. The pressure receiving portion 510 includes a diaphragm part 511 that is bent by a pressure, an aluminum (Al) total reflection mirror 512, a mesa portion 513 that flattens and supports the total reflection mirror 512, and a spacer portion 514. The pressure receiving portion 510 forms a Fabry-Perot interferometer. In order to reduce a load from a side surface of the diaphragm part 511, a tip portion may be protected by a polyimide tube. Materials and sizes of the first pressure sensor 50A, the first tube 51A, the second tube 51B, and the air discharging tube 60 are examples, and the invention is not limited thereto.

Figure 19:
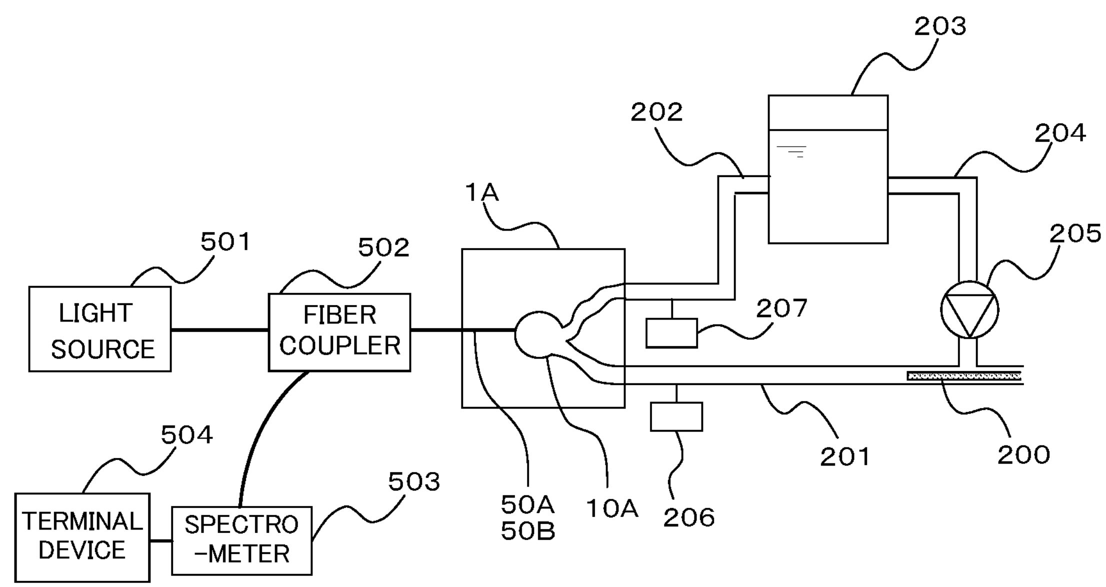
FIG. 19 is a schematic configuration diagram of a measurement system using the blood vessel model unit according to the second embodiment.

FIG. 19 is a schematic configuration diagram of a measurement system 100A using the blood vessel model unit 1A according to the present embodiment. As shown in FIG. 19, the measurement system 100A according to the present embodiment includes the blood vessel model unit 1A, the insertion pipe 201 that is the same as the insertion pipe according to the first embodiment, the first pipe 202, the water storage unit 203, the second pipe 204, the pump 205, the inlet sensor 206, and the outlet sensor 207. The measurement system 100A further includes a light source 501 connected to the first pressure sensor 50A and the second pressure sensor 50B, a fiber coupler 502, a spectrometer 503, and a terminal device 504 such as a PC.

Similar to the first embodiment, the pump 205 circulates water in the water storage unit 203 in an order of the second pipe 204, the insertion pipe 201, the blood vessel model 10, and the first pipe 202 when a measurement is performed in the measurement system 100A. The water pressure at this time is controlled based on measurement results of the inlet sensor 206 and the outlet sensor 207 so as to be substantially the same as the blood pressure. Then, the catheter 200 is inserted from an end portion of the insertion pipe 201, and the coil is placed in the aneurysm-like portion 12 of the blood vessel model 10A. Pressure in the aneurysm-like portion 12 at this time is measured by the first pressure sensor 50A and the second pressure sensor 50B.

Specifically, white light is supplied from the light source 501 to the first pressure sensor 50A and the second pressure sensor 50B. The light supplied to the first pressure sensor 50A and the second pressure sensor 50B is reflected for multiple times between the half mirror 522 and the total reflection mirror 512. Here, in the first pressure sensor 50A and the second pressure sensor 50B, the diaphragm part 511 which serves as a pressure receiving surface is bent corresponding to a pressure from outside, and a distance (cavity length) between the half mirror 522 and the total reflection mirror 512 changes. Accordingly, an optical path difference between light reflected from both mirrors changes. Light reflected from the first pressure sensor 50A and the second pressure sensor 50B is sent to the spectrometer 503 through the fiber coupler 502, and the spectrometer 503 optically detects a change in the optical path difference between the reflected light. Then, the terminal device 504 calculates the pressure according to a spectroscopic result and displays a measurement result.

Figure 20:
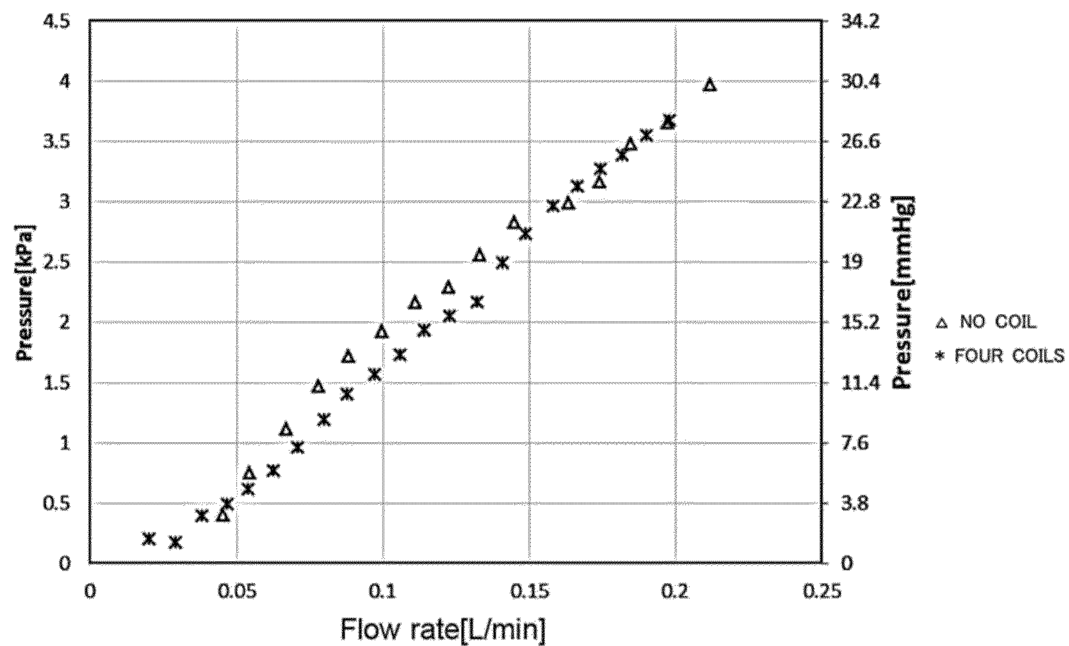
FIG. 20 is a diagram showing an example of a measurement result of a first pressure sensor.
Figure 21:
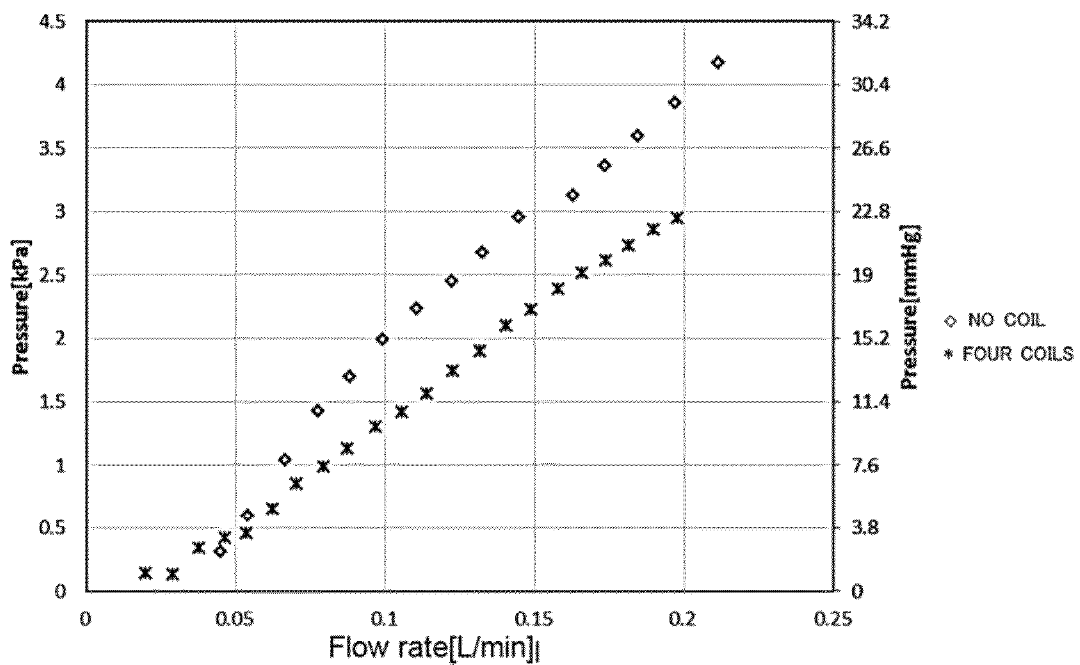
FIG. 21 is a diagram showing an example of a measurement result of a second pressure sensor.

FIG. 20 is a diagram showing an example of the result of measurement with the first pressure sensor 50A. FIG. 21 is a diagram showing an example of the result of measurement with the second pressure sensor 50B. In FIGS. 20 and 21, the horizontal axis represents the flow rate of water circulated in the blood vessel model 10A, and the vertical axis represents the pressure value measured with one of the first pressure sensor 50A and the second pressure sensor 50B. FIGS. 20 and 21 show measurement results obtained when the aneurysm-like portion 12 is not embolized and when the aneurysm-like portion 12 is embolized using four coils. FIGS. 20 and 21 indicate that for both the first pressure sensor 50A and the second pressure sensor 50B, the slope tends to be smaller when the aneurysm-like portion 12 is embolized than when the aneurysm-like portion 12 is not embolized. This suggests that the embolization of the aneurysm-like portion 12 with coils may diminish the increase in the pressure in the cerebral aneurysm with increasing flow rate of water circulated in the blood vessel model 10A. This may be because the coils serve as dampers and more coils are more effective as dampers.

It can be seen from FIGS. 20 and 21 that the aneurysm-like portion 12 may not be sufficiently embolized even when four coils are used for embolization. It can be seen from a difference between the measurement results of FIGS. 20 and 21 that the embolization is effective at a place where the second pressure sensor 50B is placed while the embolization is not effective and the coil may be placed in a biased manner at a place where the first pressure sensor 50A is placed.

As described above, a state in the aneurysm-like portion 12 can be quantified by measuring the pressure in the aneurysm-like portion 12 of the blood vessel model 10A that reproduces an aneurysm in the present embodiment. Then, a skill level of a doctor or an effect of an embolization treatment can be evaluated from the state of the aneurysm-like portion 12. Although two pressure sensors are provided according to the above description, the number of pressure sensors may be one or three or more. The measurement system can be used not only for an aneurysmal coil embolization, but also for a treatment such as a treatment of placing a stent in a neck portion of an aneurysm and an embolization treatment of Arteriovenous Malformation (AVM), and for a safety or effectiveness experiment at the time of developing various medical devices.

A pressure sensor may be provided at a place other than the aneurysm-like portion 12 of the blood vessel model 10A. Pressure of blood flowing from a thick blood vessel to a thin blood vessel can be simulated by taking the first tube 51A and the second tube 51B as blood vessels and measuring a pressure of water flowing into the first tube 51A and the second tube 51B with the first pressure sensor 50A and the second pressure sensor 50B.

Next, a method for manufacturing the blood vessel model unit 1A according to the present embodiment will be described. Similar to the first embodiment, the blood vessel model unit 1A according to the present embodiment is manufactured by laminating the sacrificial material 4 and PVA which is a material of the blood vessel model 10A and the base 20 using a 3D printer.

Figure 22:
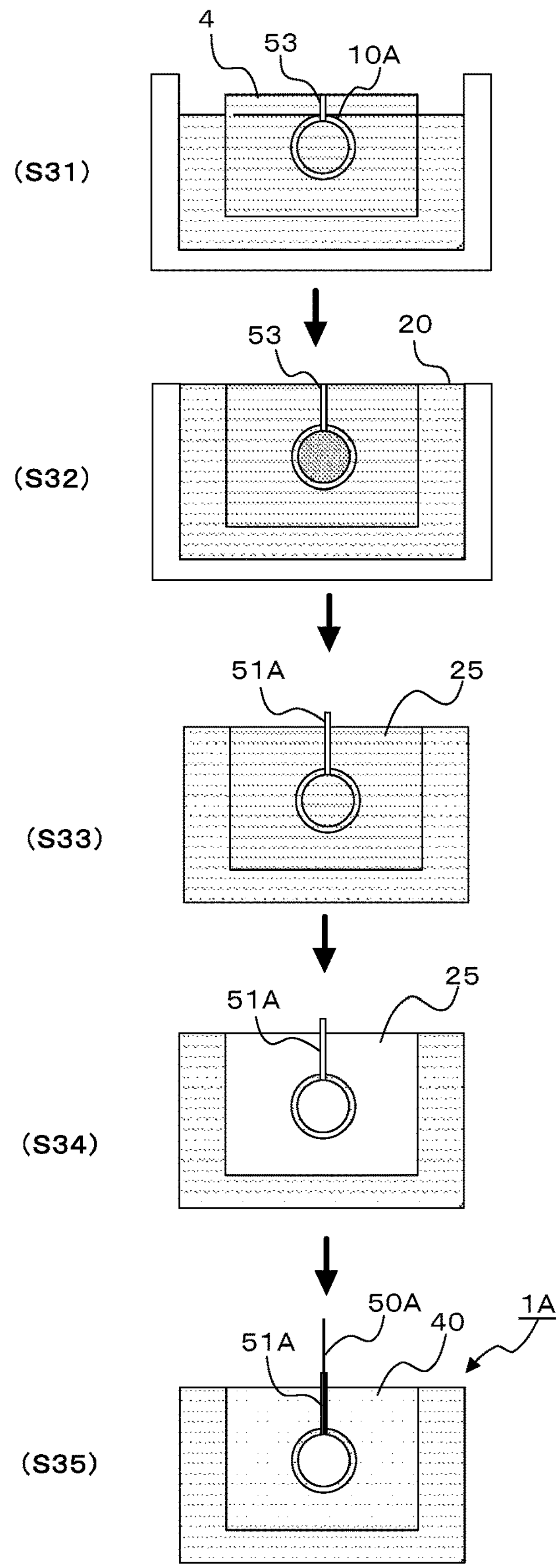
FIG. 22 is a schematic cross-sectional view showing a flow of a method for manufacturing the blood vessel model unit according to the second embodiment.

FIG. 22 is a schematic cross-sectional view showing a flow of a method for manufacturing the blood vessel model unit 1A according to the present embodiment. The method for manufacturing the blood vessel model 10A and the base 20 is similar to the method in the first embodiment. Attachment of the first pressure sensor 50A which is different from the first embodiment will be described in FIG. 22. According to the present embodiment, first, the sacrificial material 4 having a hole 53 is formed (S31 and S32). Then, the first tube 51A is inserted into the hole 53 (S33). At this time, the first tube 51A is placed against the sacrificial material 4 in a lumen of the blood vessel model 10A, so that the protruding amount of the first tube 51A can be regulated. Then, the sacrificial material 4 is removed (S34), the filler 40 is filled into the recessed part 25, and the first pressure sensor 50A is inserted into the first tube 51A (S35). The second tube 51B and the air discharging tube 60 are attached in the same manner as the first tube 51A. Accordingly, the blood vessel model unit 1A is manufactured.

Figure 23:
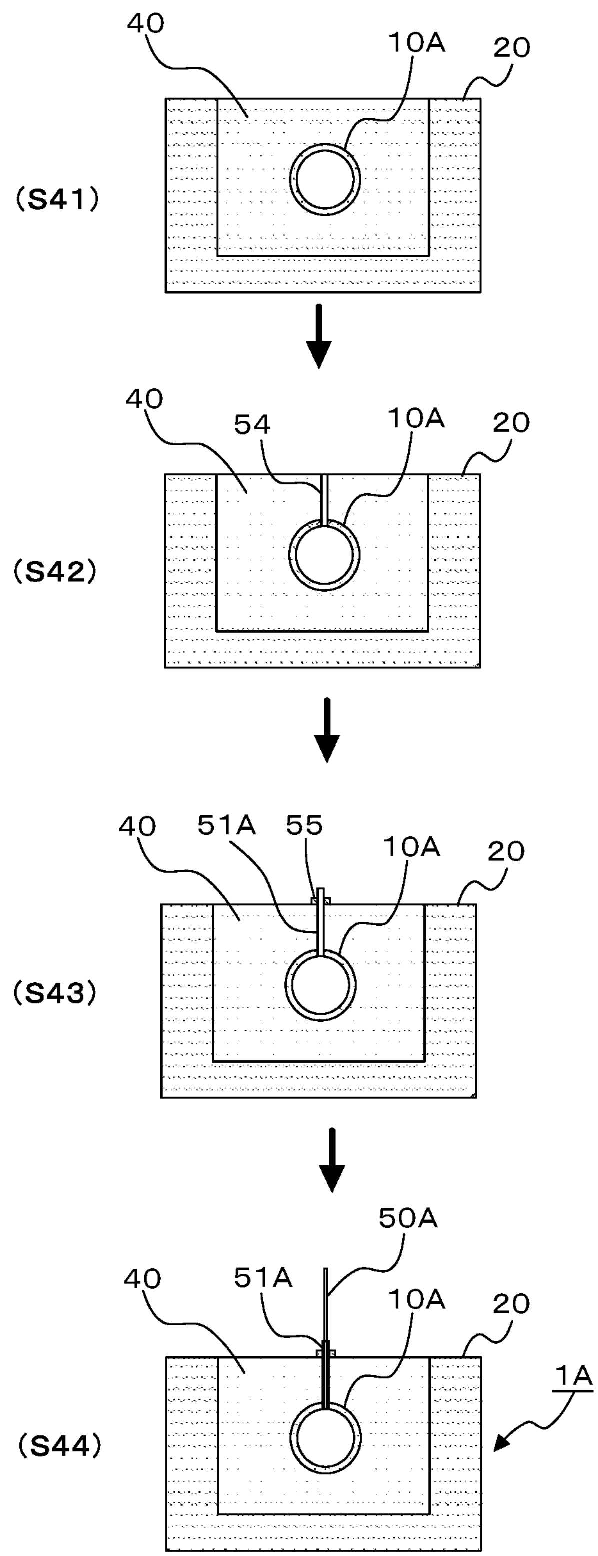
FIG. 23 is a schematic cross-sectional view showing a flow of a method for manufacturing a blood vessel model unit according to a modification of the second embodiment.

The attachment of the first pressure sensor 50A is not limited to the example in FIG. 22. FIG. 23 is a schematic cross-sectional view showing a flow of a method for manufacturing the blood vessel model unit 1A according to a modification of the present embodiment. In the modification, similar to the first embodiment, first, PVA and the sacrificial material 4 are laminated, and the sacrificial material 4 is removed, so that the blood vessel model 10A and the base 20 are formed, and the filler 40 is filled into the recessed part 25 (S41). Then, a hole 54 is formed using a needle or the like at the position to which the first pressure sensor 50A is attached (S42). The hole 54 is formed to pass through the filler 40 and an upper wall of the blood vessel model 10A.

Thereafter, the first tube 51A is inserted into the hole 54, and a gap between the hole 54 and the first tube 51A is sealed with a bond 55 such that no water leakage occurs (S43). Finally, the first pressure sensor 50A is inserted into the first tube 51A and the blood vessel model unit 1A is manufactured (S44). For example, when it is desirable to add a pressure sensor after the blood vessel model unit 1A is manufactured, the pressure sensor can be added as in the present modification.

The first tube 51A, the second tube 51B, and the air discharging tube 60 are not essential components, and may be omitted. In this case, the first pressure sensor 50A and the second pressure sensor 50B may be directly disposed in the aneurysm-like portion 12. The air discharging tube 60 may be provided in the blood vessel model unit 1 according to the first embodiment.

Third Embodiment

Figure 24:
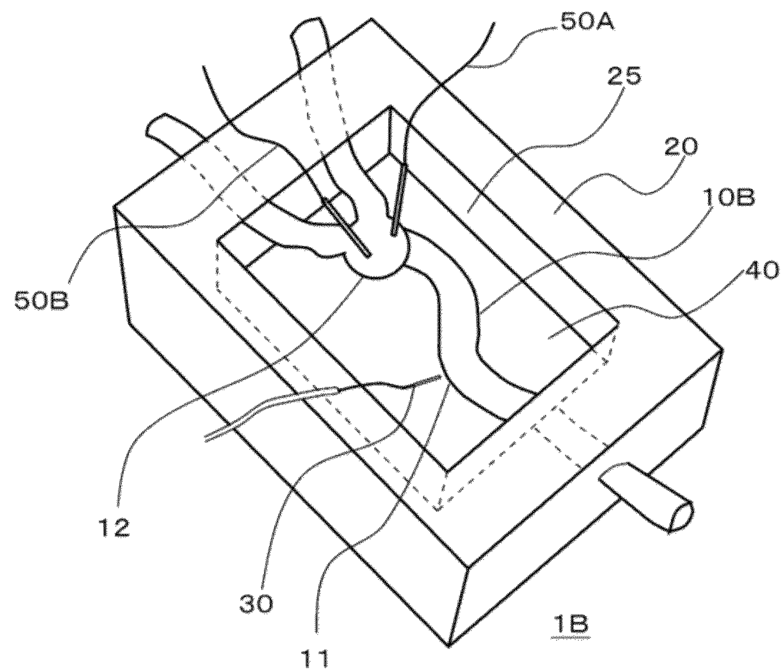
FIG. 24 is a perspective view of a blood vessel model unit according to a third embodiment.

Next, a third embodiment according to the invention will be described. A blood vessel model unit 1B according to the present embodiment is formed by combining the first embodiment and the second embodiment. FIG. 24 is a perspective view of the blood vessel model unit 1B according to the present embodiment. As shown in FIG. 24, a blood vessel model 10B in the blood vessel model unit 1B according to the present embodiment includes the bent portion 11 and the aneurysm-like portion 12. The blood vessel model unit 1B according to the present embodiment includes the displacement sensor 30 used for measuring the displacement of the bent portion 11, and the first pressure sensor 50A and the second pressure sensor 50B used for measuring the pressure in the aneurysm-like portion 12.

Other configurations of the blood vessel model unit 1B and configurations of the displacement sensor 30, the first pressure sensor 50A and the second pressure sensor 50B are the same as the configurations in the first and second embodiments.

According to the present embodiment, the displacement and an internal pressure of the blood vessel model unit 1B can be measured, and the blood vessel model unit 1B can be used in training for a plurality of treatments, evaluation of the training, and a safety or effectiveness experiment at the time of developing medical devices.

Fourth Embodiment

Figure 25:
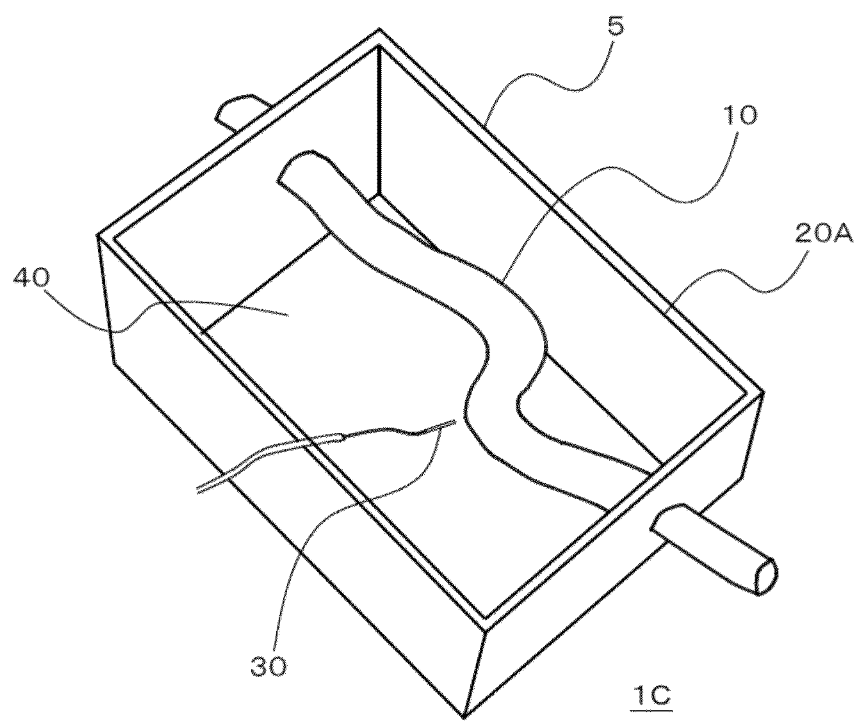
FIG. 25 is a perspective view of a blood vessel model unit according to a fourth embodiment.

Next, a fourth embodiment according to the invention will be described. A blood vessel model unit 1C according to the present embodiment is different from the first embodiment in the configuration of the base 20. FIG. 25 is a perspective view of the blood vessel model unit 1C according to the present embodiment. As shown in FIG. 25, the blood vessel model unit 1C according to the present embodiment includes a box-shaped base 20A formed of acryl. The filler 40 is filled in the base 20A, and the blood vessel model 10 and the displacement sensor 30 are disposed in the base 20A.

According to the present embodiment, the blood vessel model unit 1C can be prevented from deformation by using acryl as the base.

Although embodiments of the invention have been described above, the invention is not limited to configurations in the above embodiments, and various modifications or combinations is possible within the spirit of the technique of the invention. For example, a blood vessel is described as an example of a hollow organ in the above embodiments. Alternatively, the invention can also be applied to a model unit of other hollow organs such as a bile duct. The displacement sensor 30 is not limited to an ultrasonic sensor, and may be an optical sensor or the like. The first pressure sensor 50A and the second pressure sensor 50B are not limited to the fiber-optic pressure sensor, and may be a pressure sensor or the like using an electrical characteristic. Further, any number of displacement sensors 30 may be appropriately provided to measure the displacement of any portion other than the bent portion 11 in the blood vessel model 10. Any number of pressure sensors may be disposed at any portion where the pressure needs to be confirmed other than the aneurysm-like portion 12 of blood vessel model 10. Any number of air discharging tubes 60 may be appropriately provided at places where air is likely to accumulate in the blood vessel model 10.

The displacement sensor 30 which is an ultrasonic sensor may be used to measure the flow rate in the blood vessel model 10. In this case, a fluid containing a powder that simulates red blood cells is circulated in the blood vessel model 10. Then, a speed of the powder contained in the fluid in the blood vessel model 10 can be calculated and the flow rate from a cross-sectional area of the blood vessel model 10 can be calculated based on a measurement result of the displacement sensor 30. Although the blood vessel model 10 serves as a measurement target in the above example, the invention is not necessarily limited to a blood vessel and can be applied to a hollow organ model. In this case, the displacement sensor 30 (the ultrasonic sensor) can be used to measure a flow rate of the liquid flowing inside the hollow organ model. Furthermore, the powder is not limited to the one that simulates red blood cells.

The methods for manufacturing the blood vessel model unit in the above embodiments are just examples, and the blood vessel model unit according to the invention may be manufactured by other methods.

REFERENCE SIGN LIST

1, 1A, 1B, 1C blood vessel model unit
3 mold frame
4 sacrificial material
6 support material
10, 10A, 10B blood vessel model
11 bent portion
11*a* first outer wall
11*b* first inner wall
11*c* second inner wall
11*d* second outer wall
12 aneurysm-like portion
20, 20A base
25 recessed part
30 displacement sensor
40 filler
50A first pressure sensor
50B second pressure sensor
51A first tube
51B second tube
52 hot bond
53, 54 hole
55 bond
60 air discharging tube
61 hot bond
100, 100A measurement system
200 catheter
201 insertion pipe
202 first pipe
203 water storage unit
204 second pipe
205 pump
206 inlet sensor
207 outlet sensor
301 pulsar receiver
302 oscilloscope
310 sensor unit
311 ultrasonic vibrator
312 first electrode
313 second electrode
314 backing
320 wiring unit
321 film
322 first electrode pad
323 first wire
324 second electrode pad
325 second wire
326 first conductive material
327 second conductive material
328 insulating material
501 light source
502 fiber coupler
503 spectrometer
504 terminal device
510 pressure receiving portion
511 diaphragm unit
512 total reflection mirror
513 mesa portion
514 spacer portion
520 optical fiber portion
521 optical fiber
522 half mirror

The invention claimed is:

1. A hollow organ model unit comprising:

a base that has a recessed part;

a hollow organ model that is placed in the recessed part;

a filler that is filled in the recessed part; and an ultrasonic sensor configured to measure a displacement of the hollow organ model, wherein the hollow organ model has a bent portion, and the ultrasonic sensor is placed in the filler, outside and away from the bent portion and measures a displacement of the bent portion.

2. The hollow organ model unit according to claim 1, further comprising:

an air discharging tube configured to discharge an air in the hollow organ model.

3. The hollow organ model unit according to claim 1, further comprising:

an ultrasonic sensor configured to measure fluid speed flowing in the hollow organ model.

4. The hollow organ model unit according to claim 1, further comprising:

a support material that supports the sensor or the hollow organ model.

5. The hollow organ model unit according to claim 1, wherein the hollow organ model comprises polyvinyl alcohol, and the filler comprises water or polyvinyl alcohol.

6. The hollow organ model unit according to claim 5, wherein the polyvinyl alcohol that forms the hollow organ model has a concentration of 10 wt % to 20 wt %.

7. The hollow organ model unit according to claim 5, wherein the polyvinyl alcohol that forms the filler has a concentration of 2 wt % to 10 wt %.

8. A hollow organ model unit comprising:

a base that has a recessed part;

a hollow organ model that is placed in the recessed part;

a filler that is filled in the recessed part;

a fiber-optic pressure sensor configured to measure a pressure in the hollow organ model, and a tube into which the fiber-optic pressure sensor is inserted, wherein the hollow organ model has an aneurysm-like portion, the fiber-optic pressure sensor measures a pressure inside the aneurysm-like portion, and the tube is disposed so that an end portion at one side of the tube passes through a wall of the aneurysm-like portion and protrudes towards an inner side of the aneurysm-like portion.

9. A method for manufacturing a hollow organ model unit which comprises a base that has a recessed part, a hollow organ model that is placed in the recessed part, a filler that is filled in the recessed part, and a sensor configured to measure a displacement of the hollow organ model, a pressure in the hollow organ model, or fluid speed flowing in the hollow organ model, the method comprising:

laminating polyvinyl alcohol and a sacrificial material to form the hollow organ model and the base;

positioning the sensor midway through laminating the polyvinyl alcohol and the sacrificial material;

removing the sacrificial material; and filling the filler into a recessed part formed by removing the sacrificial material.

10. The manufacturing method according to claim 9, wherein the sacrificial material is a wax, limonene, polyethylene glycol, or polyvinyl alcohol.

11. The manufacturing method according to claim 9, wherein the sensor or the hollow organ model is positioned using the sacrificial material and a support material.

* * * * *